United States Patent
Kumar et al.

(10) Patent No.: US 6,208,884 B1
(45) Date of Patent: Mar. 27, 2001

(54) NONINVASIVE ROOM TEMPERATURE INSTRUMENT TO MEASURE MAGNETIC SUSCEPTIBILITY VARIATIONS IN BODY TISSUE

(75) Inventors: Sankaran Kumar, San Marcos; William F. Avrin, San Diego, both of CA (US)

(73) Assignee: Quantum Magnetics, Inc., San Diego, CA (US)

( * ) Notice: Subject to any disclaimer, the term of this patent is extended or adjusted under 35 U.S.C. 154(b) by 0 days.

(21) Appl. No.: 09/135,890

(22) Filed: Aug. 18, 1998

Related U.S. Application Data

(63) Continuation-in-part of application No. 08/670,393, filed on Jun. 25, 1996, now Pat. No. 5,842,986.

(51) Int. Cl.$^7$ ........................................................ A61B 5/05
(52) U.S. Cl. ...................... 600/409; 324/260; 324/207.21
(58) Field of Search ...................................... 600/407, 409, 600/410; 324/260, 261, 207.11, 207.12, 207.13, 207.14, 207.15, 207.16, 207.17, 207.18, 207.19, 207.21

(56) References Cited

U.S. PATENT DOCUMENTS

| | | | |
|---|---|---|---|
| 4,431,005 | 2/1984 | McCormick | 128/656 |
| 4,709,213 | 11/1987 | Padhrasky | 324/329 |
| 4,801,882 | * 1/1989 | Daalmans | 324/248 |

(List continued on next page.)

OTHER PUBLICATIONS

C.M. Bastuscheck, "Technique for Measuring the AC Susceptibility of Portions of the Human Body or Other Large Objects," J. Appl Phys. 58 (10), pp. 3896–3906 (1985).

F.M. Bryden, "Real Time Ultrasound in the Assessment of Intraocular Foreign Bodies," Eye 4, pp. 727–731 (1990).

E. Costa Monteiro, "Magnetic Measurement Techniques for Locating Foreign Bodies in Humans," Tenth International Conference on Biomagnetism, p. 314 (1996).

(List continued on next page.)

Primary Examiner—Marvin M. Lateef
Assistant Examiner—Eleni Mantis Mercader
(74) Attorney, Agent, or Firm—Baker & Maxham

(57) ABSTRACT

A probe instrument using room-temperature sensor(s) that can measure magnetic susceptibilities variations. The instrument has sufficient resolution to monitor paramagnetic materials in a human body, and preferably iron in a human liver by noninvasively examining patients with iron-overload diseases. The instrument includes room temperature magnetic sensors, and detects the sample, that is the tissue response to an alternating current field applied by an applied field coil. The sensors that can be used include magnetoresistive, fluxgate and magnetoinductive sensors. The applied field coil dimensions are chosen so that the applied field is optimized for maximum response from the liver while minimizing the effects due to the overlying abdominal tissue and at the same time not unduly increasing the sensitivity of the instrument to the lung. To minimize noise introduced in the sensor due to fluctuations in the applied field, the applied field is canceled at the position of the sensor, i.e. the real and imaginary parts of the applied field are canceled. To overcome variations in the sensor output due to fluctuations in the applied field, change in the ambient temperature and mechanical relaxation of the instrument, the sensor-sample distance is modulated. The detector assembly is oscillated while the examined patient remains stationary. The detector's applied field coil is fabricated on a printed circuit board and is attached firmly to a solid nonmetallic support structure forming part of a detector. This improves mechanical and thermal stability, and makes for a precise and inexpensive fabrication of the applied field coil. The detector assembly forms part of a probe instrument for performing noninvasively the paramagnetic concentration of a patient.

42 Claims, 6 Drawing Sheets

U.S. PATENT DOCUMENTS

| | | | |
|---|---|---|---|
| 4,827,217 | * 5/1989 | Paulson | 324/248 |
| 4,969,469 | * 11/1990 | Mills | 128/653 |
| 5,057,095 | 10/1991 | Fabian | 604/362 |
| 5,099,845 | 3/1992 | Besz et al. | 128/653 |
| 5,105,829 | 4/1992 | Fabian et al. | 128/899 |
| 5,107,862 | 4/1992 | Fabian et al. | 128/899 |
| 5,188,126 | 2/1993 | Fabian et al. | 128/899 |
| 5,190,059 | 3/1993 | Fabian et al. | 128/899 |
| 5,233,992 | * 8/1993 | Holt et al. | 128/653.2 |
| 5,268,165 | * 12/1993 | Hedlund et al. | 424/9 |
| 5,305,751 | * 4/1994 | Chopp et al. | 128/654 |
| 5,322,682 | * 6/1994 | Bartzokis et al. | 424/9 |
| 5,353,807 | 10/1994 | DeMarco | 128/772 |
| 5,384,109 | * 1/1995 | Klaveness et al. | 424/9 |
| 5,408,178 | * 4/1995 | Wikswo et al. | 324/201 |
| 5,425,382 | 6/1995 | Golden et al. | 128/899 |
| 5,456,718 | 10/1995 | Szymaitis | 623/11 |
| 5,494,033 | 2/1996 | Buchanan et al. | 128/653 |
| 5,558,091 | 9/1996 | Acker et al. | 128/653 |
| 5,686,836 | * 11/1997 | Sasada et al. | 324/244 |
| 5,735,279 | * 4/1998 | Klaveness et al. | 128/654 |
| 5,842,986 | * 12/1998 | Avrin et al. | 600/407 |

OTHER PUBLICATIONS

E.J. Finn, "Ferromagnetic Materials in Patients: Detection Before MR Imaging," Radiology 156, pp. 139–141 (1985).

R.E. Greenblatt, "Probablistic Reconstruction of Multiple Sources in the Bioelectromagnetic Inverse Problem," Inverse Problems 9, pp. 271–284 (1982).

E. Kanal, "Aneurysm Clip Testing for Ferromagnetic Properties: Clip Variability Issues," Radiology, pp. 576–578, (1995).

Mentor Corporation, "The Detector, Injection Port Detection System," Brochure, 6 pp., (1996).

D.N. Paulson, "Biomagnetic Susceptometer with SQUID Instrumentation," IEEE Transactions on Magnetics, vol. 27, No. 2, pp. 3249–3252 (1990).

D.N. Paulson, "The Hamburg Biosusceptometer for Liver Iron Quantification," Advances in Biomagnetism, pp. 497–500, (Date Unknown).

K. Sekihara, "Reduction of Brain Noise Influence in Evoked Neuromagnetic Source Localization Using Noise Spatial Correlation," Phys. Med. Biol. 39, pp. 937–946, (1993).

N. Sepulveda, "Magnetic Susceptibility Tomography for Three–Dimensional Imaging of Diamagnetic and Paramagnetic Objects," IEEE Transactions on Magnetics, vol. 30, No. 6, pp. 6062–5069, (1993).

F.G. Shellock, "Magnetic Resonance," Bioeffects, Safety and Patient Management, pp. 115–126, (1996).

N. Smith, "A High–Sensitivity Magnetoresistive Magnetometer," J. Appl. Phys. 69 (8), pp. 5082–5084 (1991).

B. Scholz, "Probability–Based Current Dipole Localization from Biomagnetic Fields," IEEE Transactions on Biomedical Engineering, vol. 41, No. 8, pp. 735–742 (1993).

W.M. Wynn, "Advanced Superconducting Gradiometer/Magnetometer Arrays and a NOvel Signal Processing Technique," IEEE Transactions on Magnetics, vol. MAG–11, No. 2, pp. 701–707, (1974).

* cited by examiner

MR sensor in low-field region between current sheets.

NONINVASIVE ROOM TEMPERATURE INSTRUMENT TO MEASURE MAGNETIC SUSCEPTIBILITY VARIATIONS IN BODY TISSUE

CROSS-REFERENCE TO RELATED APPLICATIONS

This application is a continuation in part of parent application Ser. No. 08/670,393, entitled "Ferromagnetic Foreign Body Screening Method and Apparatus," filed Jun. 25, 1996, now, U.S. Pat. No. 5,842,986 and incorporated herein by reference, which describes an apparatus and method for noninvasive localized detection of foreign ferrous metallic object(s) in a patient.

The U.S. Government has a paid-up license in this invention as provided for by the terms of Contract No. N 43-DK-7-2250 awarded by the National Institutes of Health.

BACKGROUND

1. Field of the Invention

This invention relates generally to an instrument using room-temperature sensors that measure magnetic susceptibility variations in the body. In particular, the instrument can monitor naturally occurring iron in a human liver noninvasively.

2. Discussion of the Related Art

Millions of people suffer from diseases related to the metabolism of iron in the human body. Among these are Cooley's anemia (also known as thalassemia), sickle cell anemia, and hemochromatosis. There is a strong need for an accurate, noninvasive method to measure body iron stores to enable more effective treatments.

This need is especially acute in the case of Cooley's anemia, or thalassemia. In this disease, where the blood is deficient in hemoglobin, patients must undergo blood transfusions in order to survive. These blood transfusions must be frequent (every 2 to 4 weeks). However, the repeated transfusions create a chronic iron overload with an abnormal buildup of iron in the liver, spleen, and heart, see Bothwell, T. H., et al., (1979); Iron Metabolism in Man, Oxford: Blackwell. This iron overload must be removed continually by chelation therapy, and iron stores must be monitored regularly to maintain the desired levels see Kontoghiorghes, G. J., et al. (1990), Long-term trial with the oral iron chelator 1,2-Dimethyl-3hydroxy-pyrid-4-one, Br. J. Hematology 76, 295; Nielsen, P., et al, (1995), Liver iron stores in patients with secondary hemosideroses under iron chelation therapy with deferoxamine or deferiprone, Br. J. Hematol. 91, 827; Olivieri, N. F., et al., (1995). Iron chelation therapy with oral deferiprone in patients with thalassemia major, New England J. Med. 332, 918.

Recent studies indicate that frequent blood transfusions can prevent the occurrence of strokes in children with sickle cell anemia and a clinical alert has been issued to US physicians, see NHLBI (1997), Press release of the National Heart, Lung, and Blood Institute: "New Treatment Prevents Strokes In Children With Sickle Cell Anemia." As with thalassemic patients, sickle cell anemic patients undergoing frequent blood transfusions suffer from liver iron overload.

Hemochromatosis afflicts a significant population (0.5% of the U.S. population with European ancestry) and results in excessive amounts of iron stored in the liver. The excess iron may be reduced by periodic blood withdrawals from the body. Monitoring iron stores is important to determine the well being of the patient and the course of treatment (such as the frequency of blood withdrawals).

At present, there is no truly satisfactory method for routinely monitoring iron stores. Serum ferritin and urine iron excretion measurements are not accurate, because they are only indirectly related to iron stores. Liver biopsy is painful and invasive, and thus unsuitable for routine monitoring. Nuclear resonance scattering techniques as taught in an article by Wielopolsky, L., and Zaino, E. C. (1992) entitled "Noninvasive in-vivo measurement of hepatic and cardiac iron," J. Nuclear Med. 33, 1278, is generally unsuitable because it involves high doses of a radioactive isotope. Computed tomography involves high doses of X-rays, and it is only sensitive enough to detect the highest levels of iron, see Guyader, Y., et al. (1989), Evaluation of computed tomography in the assessment of liver iron overload, Gastroenterology 97, 737.; and Nielsen, P., et al. (1992), Noninvasive liver-iron quantification by computed tomography in iron over loaded rats, Investigative Radiology 27, 312. Magnetic resonance imaging has been used to assess iron stores, but gives inaccurate results at the higher liver iron concentrations, see Kaltwasser, J. P., et al. (1990), Noninvasive quantification of liver iron overload by magnetic resonance imaging, Br. J. Hematology 74, 360; Engelhardt, R., et al. (1994), Liver iron quantification, Mag. Res. Imaging 12, 999.; and Nielsen, P., et al. (1995), Liver iron stores in patients with secondary hemosideroses under iron chelation therapy with deferoxamine or deferiprone, Br. J. Hematol. 91, 827.

Biomagnetic susceptometry is a diagnostic procedure that involves noninvasive, radiation-free, direct, and accurate, measurement of the magnetic susceptibility of organs and tissue within a human or animal body. Biomagnetic susceptometry can be used to measure human iron stores contained in the liver, see Harris, J. W., et al. (1978), Assessment of human iron stores by magnetic susceptibility measurements, Clin. Res. 26, 540A.; Brittenham, G. M., et al. (1993), Hepatic iron stores and plasma ferritin concentration in patients with sickle cell anemia and thalassemia major, Amer. J. Hematology 42, 85; Brittenham, G. M., et al. (1982), Magnetic susceptibility of human iron stores, New England J. Med., 307, 167 1.; Fischer, R., et al. (1992), Liver iron quantification in the diagnosis and therapy control of iron overload patients, Biomagnetism: Clinical. Aspects, M. Hoke, et al., eds., Elsevier, Amsterdam, p. 585., 1992; Fischer, R., et al. (1989), in Advances In Biomagnetism, S. J. Williamson, et al., eds., Plenum, New York, p. 501. Paulson. D. N., et al. (1991), Biomagnetic susceptometer with SQUID instrumentation, IEEE Trans. Magnetics 27, 3249.; and Nielsen, P., et al. (1995), Liver iron stores in patients with secondary hemosideroses under iron chelation therapy with deferoxamine or deferiprone, Br. J. Hematol. 91, 827. Unfortunately, the existing instruments, based on Superconducting Quantum Interference Devices(SQUIDs) are complex and expensive. They also use liquid helium, leading to significant operating costs and supply problems. Only a few such devices are in use worldwide presently due to their complexity and expense. These few instruments can serve only a tiny fraction of patients with iron-overload diseases. Thus, there is a need for a simpler, less expensive liver probing instrument using biosusceptometer concepts that can be installed in every major population center.

SQUIDs based on the recently developed High-Temperature Superconductors (HTS) could, in principle, reduce the cost of biomagnetic suceptomety. HTS SQUIDs, which can operate at liquid-nitrogen temperatures, would reduce operating costs, and some of the equipment costs, compared to SQUID devices operating at liquid helium temperatures. However, even at liquid-nitrogen temperatures, the operating costs would be higher than those of ordinary instruments operating at room temperature. Moreover, HTS-SQUIDs are expensive to construct and use, because of the difficulty and low yield of the fabrication process. The difficulties, and the costs, are compounded because these devices are vulnerable to moisture, thermal cycling, and static electrical discharge. HTS-SQUIDs also require the same expensive electronics as conventional SQUIDs.

The instant invention obviates the need for cryogenically cooled SQUIDs by providing operational use at room temperature, making for much less expensive fabrication and use. The invention allows, generally, for measurements of variations of magnetic susceptibility in a patient and, in particular, for an accurate and inexpensive way of monitoring liver iron in patients. In addition, certain improvements introduced in this invention are applicable to all types of magnetic susceptibility measurements.

SUMMARY OF THE INVENTION

Broadly speaking, this invention provides a practical method and apparatus for measuring variations of magnetic susceptibilities in body tissue and, in particular, preferably iron concentration in a patient's liver. The probing instrument's distal end assembly includes a room temperature functioning magnetic sensor that can detect the characteristic magnetic response from tissue to an applied alternating current (AC) magnetic field supplied by an applied-field coil that is also part of the instrument's distal end assembly. The magnetic susceptibility measurements have sufficient resolution to monitor iron in the liver, when the instrument is placed external to the patient.

The magnetic sensor can be, but is not necessarily limited to, a magnetoresistive sensor (including giant magnetoresistive and spin-dependent tunneling sensors), a fluxgate magnetometer, or a magneto-inductive sensor. The applied field coil dimensions are such that an applied field is optimized for maximum response from localized tissue areas, such as organs, in the body. In particular, the instrument is preferably designed for monitoring iron in the liver. For this application, the applied field coil dimensions are optimized to maximize the magnetic susceptibility response from the liver and minimize effects caused by the overlying abdominal tissue, while not unduly increasing the sensitivity of the probe instrument due to a lung being in close proximity to the liver. To minimize noise introduced in the magnetic sensor due to fluctuations in the applied field, the applied field is canceled at the position of the sensor. Both the real and imaginary parts of the applied field are canceled. To overcome variations in the sensor output caused by changes in ambient temperature and mechanical relaxation of the instrument, the sensor-sample distance is modulated by oscillating the detector assembly. In contrast with conventional biomagnetic measurement instruments that use SQUID sensors, where a patient is moved relative to the instrument, the proposed invention's magnetic sensor is moved relative to the patient. The instrument's detector assembly has an applied field coil fabricated on a printed circuit (PC) board that is attached to a solid nonmetallic support base which in turn attaches to an oscillatory member which displaces the detector assembly when used for examining a patient.

The probe instrument's distal end detector assembly has a geometrically designed applied field coil using either multiple parallel-sheet coils or a substantially coplanar applied field coil of concentric design. The magnetic sensor is preferably a magnetoresistive (MR) sensor. When an MR sensor is used, a feedback coil is mounted on the sensor, which "locks" the sensor at its optimum operating point by applying a compensating field to cancel changes in the ambient field, thus maintaining a constant sensitivity of the detector assembly.

The probing instrument's magnetic sensor control electronics, a motor/crank rod arrangement for oscillatory movement of the instrument's distal end detector assembly, an applied field AC-field source signal generator, a lock-in amplifier, an audio amplifier, and an FFT spectrum analyzer or equivalent computer device for signal analysis can all be incorporated in a single medical instrument housing for field use.

A physician uses the probing instrument by positioning the probe's distal end on a patient's abdomen, and the instrument's detector assembly is preferably oscillated over the organ, and specifically over the liver area in preferred use. The probe instrument then analyzes the observed signal, and outputs data corresponding to material of interest and preferably paramagnetic material concentration such as iron when the instrument is used as an iron probing instrument.

BRIEF DESCRIPTION OF THE DRAWINGS

The objects, advantages and features of this invention will become readily apparent from the detailed description, when read in conjunction with the accompanying drawing, in which.

DETAILED DESCRIPTION OF THE PREFERRED EMBODIMENTS

Figure 1:
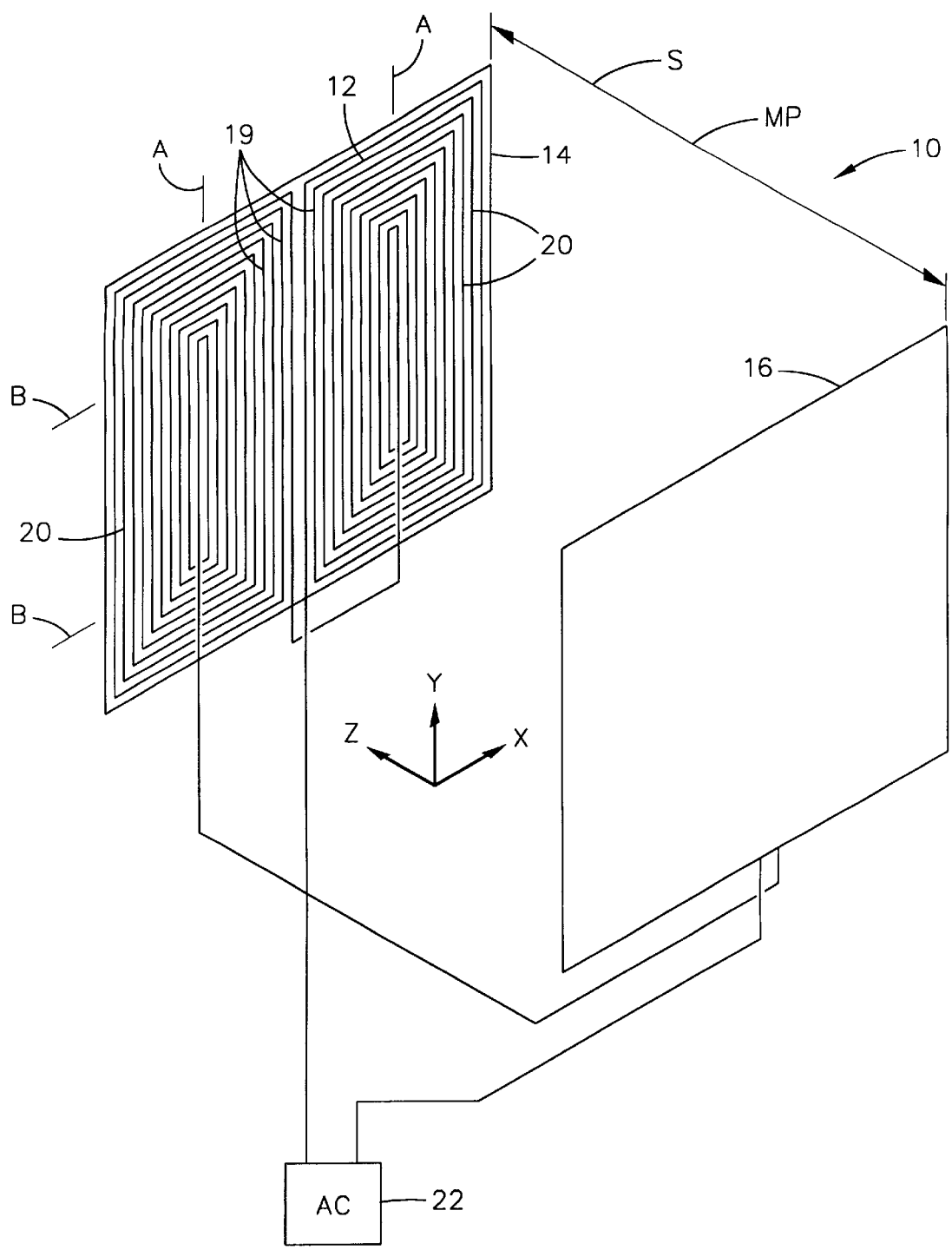
FIGS. 1, 2 and 3 show features of a magnetic susceptibility detector, which includes the applied field coil(s) with a magnetic sensor(s), as disclosed in parent U.S. patent application Ser. No. 08/670,393.

Provided herein is a room-temperature medical probing instrument that measures variations of magnetic susceptibility. In particular, an exemplary liver probing instrument is provided that has sufficient resolution to monitor liver iron in patients. The invention's probe instrument can make magnetic susceptibility measurements with an uncertainty corresponding to a liver-iron concentration of about 30 micrograms per milliliter. This instrumental resolution is roughly ten times lower than the normal liver iron concentration, and thirty times lower than the iron concentration typically maintained in patients undergoing iron chelation therapy. Thus, an inexpensive room-temperature biomagnetometer, as discussed below, provides routine, cost-effective, non-invasive monitoring of iron in a patient's liver or other paramagnetic material as one preferred device.

The noise of the room-temperature instrument is small compared to the uncertainties (typically 200–500 micrograms/ml) that are actually achieved in liver-iron measurements on real patients. These uncertainties are caused mainly by the magnetic response of tissues between the liver and the abdominal surface. For a room temperature system, as for existing instruments based on SQUID sensors, this abdominal tissue effect, and not the noise in the magnetic sensors, determines the precision of liver-iron measurement. Because the crucial limitation in the sensitivity of the liver-iron measurement is imposed by the tissue response rather than the noise of the sensor itself, the somewhat higher noise of the room temperature functioning magnetic sensor compared to a SQUID is not a limiting factor in the performance of the instrument.

Performance of the room-temperature liver instrument depends on two critical issues:

a) The instrument has to be sensitive enough to see the small magnetic signals produced by the magnetic susceptibility of the liver and b) The liver susceptibility has to be determined accurately in the presence of the interfering signal produced by the slight magnetic susceptibility of the abdominal wall and other surrounding tissues such as the lung.

In magnetic susceptibility measurements, a magnetic field is applied, inducing a magnetization in the tissue area of interest. A small magnetic field produced by this sample magnetization is then detected using a magnetic sensor. At low applied field, the sample magnetization is proportional to the intensity of the applied field and to the magnetic susceptibility of the sample, that is the tissue.

In liver susceptometry, very weak susceptibilities are encountered. The difference in magnetic susceptibility between the liver and surrounding tissue is proportional to the liver iron concentration. The main iron compound stored in the liver has a susceptibility of approximately $1.6 \times 10^{-6}$ (in SI units) per milligram of iron per cubic centimeter of liver. Typical patients with iron overload have several milligrams of iron per cubic centimeter of liver. The instrumental noise of existing SQUID biosusceptometers corresponds to an uncertainty of about 20 micrograms per cubic centimeter in liver iron concentration. Factors including uncertainty in the magnetic susceptibility of surrounding tissues contribute sources of systematic uncertainty in clinical liver measurements. Clinical measurements with existing SQUID-based instruments achieve uncertainties in the range of 0.2–0.5 milligrams of iron per gram of liver, which corresponds to a magnetic susceptibility resolution of $(3–7) \times 10^{-7}$ (SI Units).

To detect the weak magnetic response of the liver, there are two technical issues:

1. Minimization of noise in the detector's magnetic-field sensors (and, to a lesser extent, the background noise from the environment) so that detection of the magnetic response can be performed without applying excessively large fields; and 2. Ensuring that the spurious signals due to the applied fields are small compared with the desired magnetic susceptibility signal.

Sensor Noise Requirements

To measure a given magnetic susceptibility, the applied field must be large enough and the noise from the magnetic sensor must be low enough so that the magnetic susceptibility response is much greater than the sensor noise. In practice, using a room-temperature instrument, the applied field is limited by the need to avoid excessive ohmic heating in the applied field coils of the detector assembly. Excessive heat loads can induce thermal drifts in the geometry of the applied field coils. As discussed below, such drifts could affect the ability to suppress spurious signals due to the applied field. However, an applied magnetic field of roughly $10^{-3}$ T to a sample tissue does not incur excessive thermal drift effects.

If a field of $10^{-3}$ T is applied, and the magnetic field due to the response of the sample is $10^{-7}$ times the applied field, then the magnetic sensor noise must be less than $10^{-10}$ Tesla. Such noise requirements can readily be met using room-temperature functioning magnetic sensors. The preferred sensor for the invention is a magnetoresistive (MR) sensor with very low noise. Such sensors are commercially available from Honeywell, Phillips, and other companies. The MR sensor operates on the principle that the resistance of particular magnetic materials (such as permalloy, an alloy of nickel and iron) is a function of the ambient magnetic field. Changes in the magnetic field result in changes in sensor resistance which, can be measured and quantified. MR sensors developed by Kodak have noise spectral densities below 30 pT/Hz$^{1/2}$ at frequencies above 20–30 Hz. Similar noise levels are achieved by MR sensors commercially available from Honeywell. With a measurement bandwidth of 0.1 Hz (three seconds of data averaging) these sensors exhibit an RMS sensor noise of $10^{-11}$ Tesla. This noise level is ten times below an estimated liver iron signal of $10^{-10}$ Tesla. A variety of other sensor types could also meet the requirements of the present invention, including other sensors based on magnetoresistance (such as giant magnetoresistance sensors and spin dependent tunneling sensors), as well as fluxgate magnetometers and magnetoinductive sensors.

To measure magnetic signals below 100 pT, care is required to reject magnetic noise from the environment. The requirements for noise rejection are less stringent in the present invention than in the existing SQUID biosusceptometers. The SQUID systems use dc magnetic fields, and produce a dc magnetic susceptibility response. These systems convert this dc magnetic response into a time-varying magnetic signal by moving the patient up and down at a frequency of 0.5 Hz. However, even with this modulation, the measurement takes place at a rather low frequency. At such frequencies, the background noise in many environments is quite large.

The invention's room-temperature system applies an AC magnetic field at a frequency between around 25 and 2,000 hertz, and detects the magnetic response at the same frequency. At these frequencies, environmental background fluctuations are usually small, as long as noise peaks at harmonics of the power-line frequency are avoided. Magnetic signal measurements needed for the liver probe instrument are $10^7$ times smaller than the field applied to a patient's body. In making such a measurement, technical issues include the stability of the applied magnetic field, the stability of the magnetic sensors, and the geometrical stability of the magnetic-field coils and sensor array.

The proposed invention's instrument is designed so that fluctuations of the current in the applied-field coil have only a negligible effect on the magnetic measurements. The invention uses a detector assembly whose applied field coil is geometrically configured such that almost no magnetic field occurs at a location where the magnetic sensor is positioned in relation to the applied field coils. If the magnetic sensor were exposed to the full amplitude of the applied field, then the current in the field coils would have to be stable to at least one part in $10^7$ to resolve the weak magnetic signals observed in biomagnetic susceptibility measurements. However, if the detector's sensor observes only $10^{-4}$ of the field applied to the sample, the coil current can vary by as much as one part in $10^4$, and the corresponding variations in the magnetic measurements are then only $10^{-8}$ of the field applied to the sample.

Figure 2:
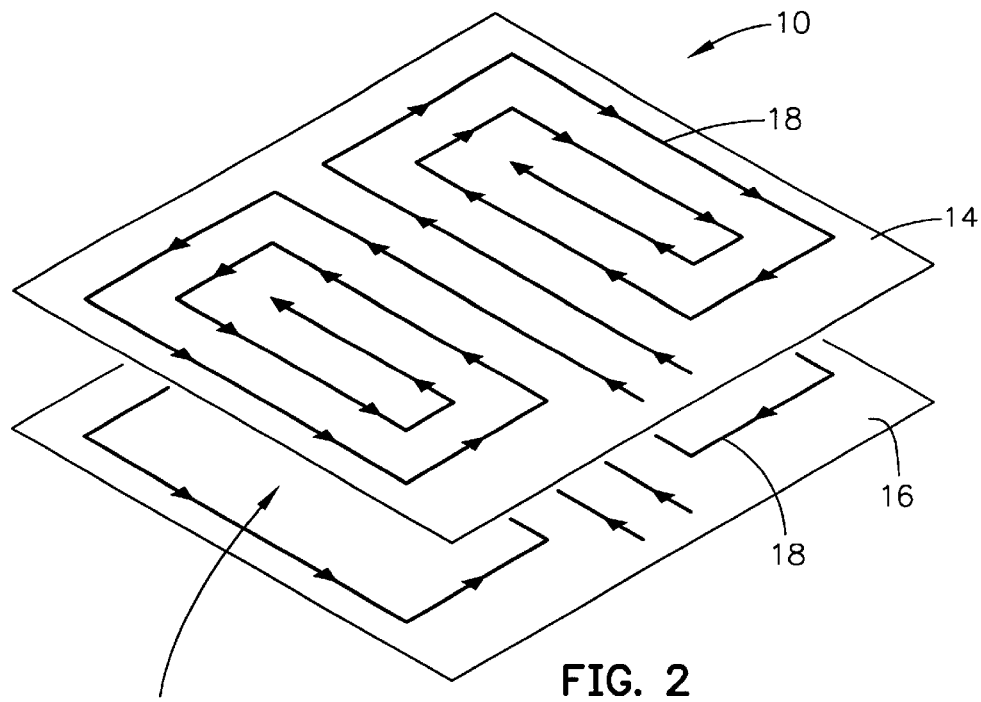
Figure 3:
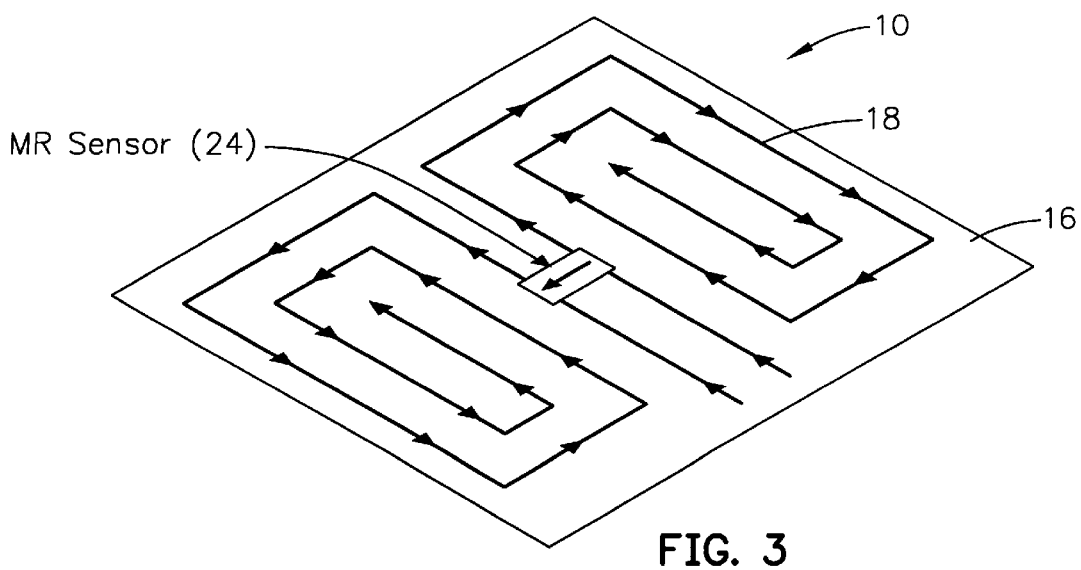

FIGS. 1, 2 and 3 show the applied field coil and magnetic sensor design and system for determining FFB object(s) as disclosed in parent U.S. patent application Ser. No. 08/670,393 of Avrin et al., entitled "Ferromagnetic Foreign Body Screening Method and Apparatus." The detector assembly 10 makes use of the technical principles discussed above. This detector assembly 10 provides magnetic susceptibility measurement information available for the detection of retained ferromagnetic foreign body (FFB) object(s), that is metallic objects inside human tissue, as a way of screening patients prior to magnetic resonance imaging (MRI) or other medical procedures. This detector assembly 10 can also be used in the invention herein for determining iron concentration content in the liver.

The invention herein teaches of another detector assembly with design improvements that improve the noise of the magnetic susceptibility measurements and optimize response from the liver with respect to an interfering signal from overlying abdominal tissue and the lung. System components also include equipment for using magnetic measurement signals from the sensors to detect and locate ferromagnetic objects, and for distinguishing the signals of the target objects from other interfering magnetic fields.

Below, the detector assembly in the parent U.S. patent application Ser. No. 08/670,393 is first described, followed by a description of the instant invention's exemplary instrument design for improved detection characteristics.

FIGS. 1, 2, and 3 collectively show a detector assembly 10 which is intended to be placed near the body region to be screened. The applied field coils 18, when supplied with a current from the current signal generator 22, generate a time-varying applied magnetic field to the body. The magnetic material in the body region responds, providing a small magnetic field that is detected by a sensor 24 (shown in FIG. 3) or array of sensors (not shown) positioned adjacent to the body region. Together, the applied field coils 18 and the sensor(s) 24 allow measurement of anomalies in the magnetic susceptibility of the body region being screened. In particular, the geometry of the applied field coils and the placement of the magnetic sensor(s) is such that the interfering applied field experienced by the magnetic sensor(s) 24 is as small as possible. As discussed earlier, this arrangement reduces the interfering signal produced by the varying magnetic field. The detector assembly consisting of the sensor(s) 24 and applied field coils 18 can be stationary, or can be movable to generate a magnetic susceptibility anomaly map over the body part being screened. The intensity and the time dependence or frequency dependence of the magnetic susceptibility anomaly can be interpreted rapidly by a signal processor to reveal the location and size of ferrous metallic objects retained within the screened body region.

The applied magnetic field may be several orders of magnitude larger than the signal of the FFB object(s). One arrangement of the device 10 is to configure the applied field coils 18 so that the applied field is nearly canceled out in regions within the device 10, within which the magnetic sensors 24 are positioned and attached (FIG. 1). The applied field coil element 12 is laid out on the surfaces of two printed circuit (PC) boards 14, 16. The two PC boards 14, 16 are placed parallel to each other, with the magnetic sensors placed between the two PC boards 14, 16. Each PC board 14, 16 accommodates a multiplicity of parallel, evenly spaced current paths 19 traveling in one direction in the center region of the board, with return paths 20 along the outer edges of the board, approximating two spiral patterns. The spiral patterns on one PC board are connected in series so that, when a current is passed through them, the resulting electric current distribution approximates a uniform sheet of current flowing in the y-direction as shown, over a substantial region near the center of the board. This region of the board is roughly defined by the area between the markers A—A and between the markers B—B. This current distribution produces a magnetic field that is nearly uniform over a region of space near the center of the board. The two boards 14, 16 of this design are placed parallel to each other, with this relationship being shown. The PC boards 14, 16 are separated by a distance S which is small compared with the length and width of the central region of uniform current. The two PC boards 14, 16 are mounted so that the current paths 19 on one board are oriented parallel to the corresponding current paths 19 on the other board. The current paths on the two boards 14, 16 are then connected in series to an AC signal generating power supply 22, so that the current flows in the same direction on both boards, the y-direction in the arrangement shown. The source 22 can be equipped with a control device, as is known in the art, to cause the field to be pulsed, to vary in frequency, or to have a waveform with multiple frequencies. These time variations in the applied field can assist in distinguishing the responsive field from the environmental background fields, by synchronization of the sensing circuitry with the power supply. In a region surrounding the centers of the two PC boards 14, 16, the magnetic field produced by this arrangement approximates that produced by a pair of parallel, uniform sheets of current flowing in the y-direction. In the space between the centers of the two PC boards, the net magnetic field is nearly zero since the contributions from the two current sheets approximately cancel each other. There is a small residual magnetic field, since perfect field cancellation is prevented by the finite size of the regions of the current sheets, and the presence of the return paths 20 along the outer edges of the PC boards 14, 16. However, due to the symmetry of the current paths in the two PC boards, the magnetic field is substantially zero in the plane midway between two PC boards. The magnetic sensor(s) 24 are placed in a plane parallel to the PC boards 14, 16, with the plane of the sensors being located at the midpoint MP between the two PC boards 14, 16, so that the sensors are nearly in a zero field state with respect to magnetic fields generated by the applied field coils 18.

FIG. 2 shows another view of the sandwiched field coil with a magnetic sensor 24, preferably an MR sensor, placed in a low-field region between parallel circuit boards 14 and 16 as shown in FIG. 1. The current paths are shown with lines and arrows. The magnetic sensor 24 is sandwiched between two printed circuit boards 14, 16. The central region of each circuit board 14, 16 contains a number of parallel, evenly spaced traces 19 which are connected in series and which carry identical applied field currents.

FIG. 3 shows where the sensor 24 is placed with respect to the applied field coil 18. The top coil has been removed to show sensor positioning. The arrow on the sensor 24 indicates the direction of its field sensitivity. Two methods are used to null out the field at the sensor location. First, a set of shims is used to adjust the position of the sensor between the two current sheets. This adjustment is needed because the applied field, given the finite size of the circuit boards 14, 16 used, is zero only on the plane of symmetry midway between the two current sheets. With this coarse adjustment, a reduced residual field occurs at the sensor to a value roughly 300 times smaller than the field at the outer surface of the coil set. A fine balance adjustment is made by placing small tabs of metal near the sensor. By using balance tabs of both steel and aluminum foil, the in-phase and the out-of-phase components are canceled out of the magnetic field with respect to the ac current supplied to the applied field coil. A reduced residual field to a level roughly 30,000 times smaller than the field at the outer surface of the coil set occurs when current is applied. Any noise due to the variations in the ac supply current is less than $10^{-8}$ of the field applied to an examined sample, that is the tissue.

In the detector 10, geometrical variation of the applied field coils 18 and sensor(s) 24 is an important effect that this field-nulling system cannot remove. Temperature variations may cause subtle distortions in the geometry of the applied-field coils, or in the position of the magnetic sensor within the coils. Such distortions can perturb the balance of the field-canceling system, producing noise in the magnetic measurements.

The detector assembly provided herein minimizes effects caused by geometric distortion of the detector assembly, by modulating a distance between a tissue of interest and the instrument's detector assembly at up to several hertz, with displacement of the detector assembly up to six inches. The change in the magnetic signal at the modulation frequency is then measured. The invention departs from methods used with conventional SQUID devices by moving the detector assembly 10 while the patient remains stationary. The instrument herein performs this function by mounting the detector assembly, which includes the applied field coils 18 and the sensor 24, on a nonmagnetic platform, and oscillating the detector assembly 10 back and forth at several hertz using a motor. The motor can drive a mechanism for producing oscillatory movement of the detector assembly. This mechanism can be a cam driven, spring biased plate, where the cam member is belt driven by the motor, or a reciprocating rod where the detector assembly is mounted to a plate that oscillates by a linear drive member. Other reciprocating motion-type devices can be used as well to provide proper oscillatory motion with displacements of up to and around six inches, at motion frequencies up to and around 10 hertz. The detector assembly is mounted in a housing that provides support and positioning for the instrument. The housing and the components of the oscillatory motion mechanism are made of nonmetallic, nonmagnetic materials. Signal analysis described below extracts information from the detector assembly's 10 signal output from the magnetic sensor 24 that preferably determines iron concentration in a patient's liver.

The ability to move the detector assembly 10 instead of the patient is significant since the overall instrument is much simpler and less expensive. Moving a SQUID type magnetic sensor is not permitted since any magnetic gradients in the environment produce signals that interfere with the direct current magnetic response measurements. These ambient magnetic gradients do not present problems in the proposed invention's measurements, since AC applied fields are used. In addition, the room temperature sensor(s) 24 have much more tolerance compared to SQUIDs when being moved in the presence of the earth's magnetic field.

Another feature of the invention is the ability to measure weak variations of the magnetic field response of tissue, preferably the liver. For optimizing signal response when observing the liver response with respect to the noise of the magnetic sensor, it is necessary that the applied field penetrate more deeply into the body than is possible with the applied field coils 18 in detector 10. Also it is desirable to maximize the magnetic response from the liver with respect to the magnetic response from the overlying abdominal tissue and from the nearby lung. Most body tissues have weak diamagnetic susceptibilities similar to that of water, roughly $-9.0 \times 10^{-6}$ in SI units. This diamagnetic response is actually 30 times greater than the $3.0 \times 10^{-7}$ SI unit that corresponds to liver iron at concentrations of around 0.2 milligrams per milliliter. The applied field coil of the present application optimizes the liver response with respect to the sensor noise and with respect to the interfering signals from the abdomen and the lung.

Figure 4:
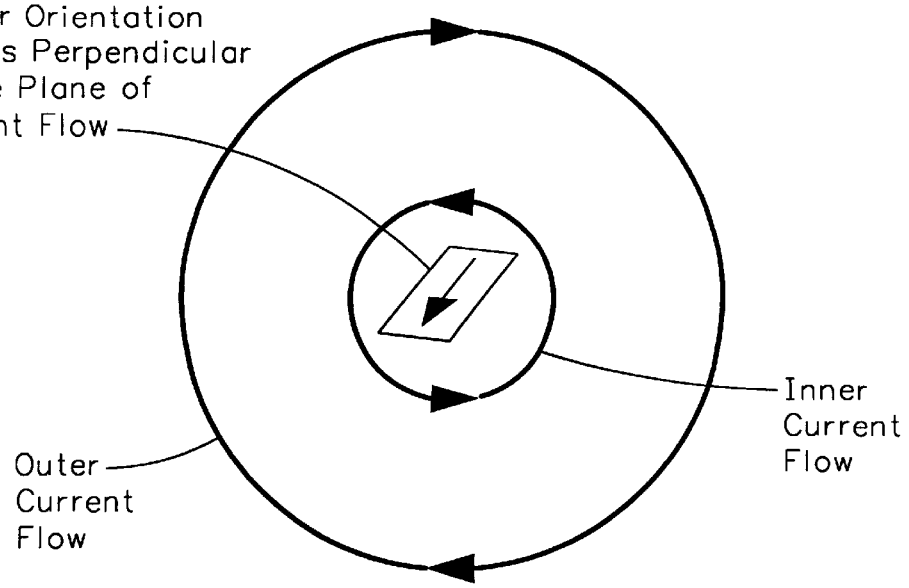
FIGS. 4, 5 and 6 show preferred features of the detector assembly, which include the preferred circular applied field coils and center mounted magnetoresistive sensor used in the probing instrument.
Figure 5:
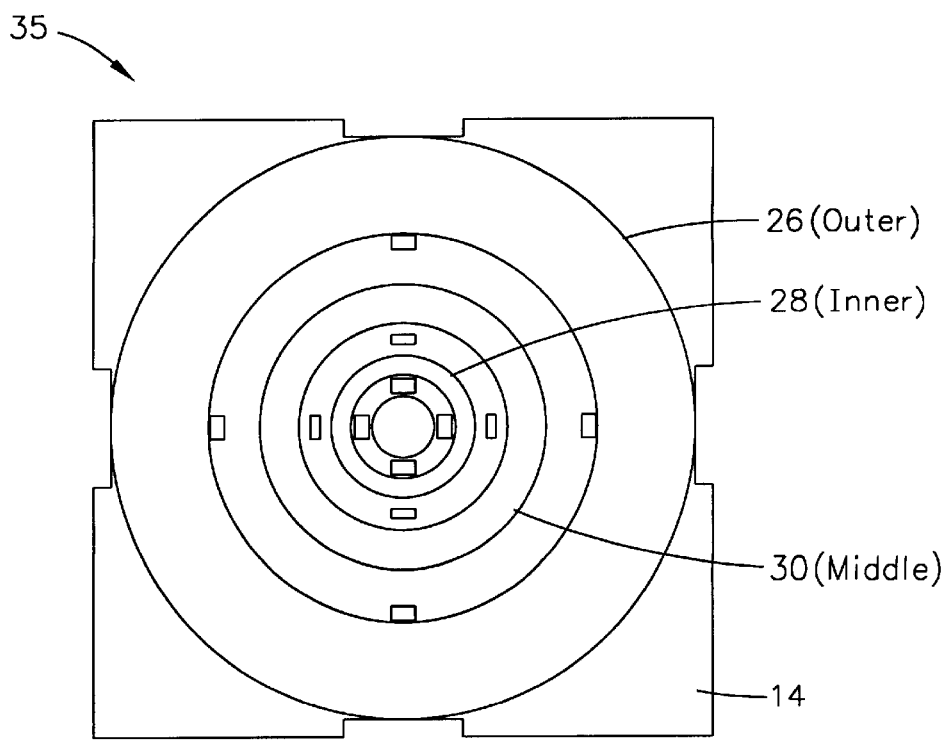

FIGS. 4 and 5 show the instant invention's design of an applied field coil arrangement 35 whose geometrical design optimizes a response signal from the liver. Such a design adjusts the diameter of the applied field coils 26,30 to control how deeply the applied AC magnetic field penetrates into the patient's body. A circular coil of radius "a" produces a field that falls off rather slowly out to distances comparable to "a," and then decays as $1/r^3$ at longer distances. The two main field coils 26,30 allow for measurement of the liver response and evaluation of the response due to the susceptibility of the overlying abdominal tissues.

FIG. 5 shows the detector assembly's applied field coil arrangement. The detector assembly comprises three concentric circular spiral coils, but can include additional coils for designs that encompass the present invention's design. FIG. 5 shows the first coil 26, with a relatively large diameter, which produces a field that reaches deep into a patient's body. The resulting magnetic susceptibility response contains contributions from both the liver iron and the abdominal tissues. The diameter of this coil 26 maximizes the liver iron contribution and minimizes the abdominal tissue contribution, so that variations in the susceptibility of the abdominal tissue have as little effect as possible on the measurement of liver susceptibility. A mean diameter in a range of around 15–50 cm for the outer coil 26 is preferred for proper measurements of a patient's liver iron.

FIG. 5 shows the small, innermost applied field coil 28. During magnetic susceptibility measurements, this smaller coil is connected in series with the outer coil 26, in such a way that the current in the inner coil 28 is in the opposite direction from that in the outer coil 26. The diameters and numbers of turns in the two coils are adjusted so that the magnetic field due to the inner coil cancels the magnetic field due to the outer coil, in a region near the common center of the two coils, producing a small zone of substantially zero magnetic field. The magnetic sensor (24 in FIG. 4) is then placed in this zone of substantially zero magnetic field so that, as discussed above, fluctuations of the current in the applied field coils produce very little noise in the magnetic susceptibility measurements. The inner coil can have a mean diameter of about 1.5 to 8 cm. Since the magnetic field due to the small, innermost coil 28 dies away rapidly with distance, the magnetic field in the patient's body tissues is produced almost entirely by the outer coil 26.

FIG. 5 also shows the intermediate-diameter coil 30 which can optionally be used, in place of the outer coil 26, to produce a magnetic field that reaches a relatively short distance into the patient's body. Magnetic susceptibility measurements made using this intermediate-diameter coil 30 will produce a magnetic susceptibility response whose main contribution comes from the patient's abdominal tissues. The results of these measurements can be used to evaluate the magnetic susceptibility of the abdominal tissues. This information can then be combined with the results of magnetic susceptibility measurements made using the outer coil 26, to evaluate the magnetic susceptibility of the liver, while removing errors due to the susceptibility of the abdominal tissues.

In magnetic susceptibility measurements made using the intermediate-diameter coil 30, the intermediate-diameter coil 30 is connected in series with the small, inner coil 28, in such a way that the magnetic field is canceled at the location of the magnetic sensor.

FIG. 5 shows exemplary dimensions of the three concentric coils that make up the applied field coil. Each coil consists of one or more concentric loops. The number of loops in each coil is proportional to its diameter. This ensures that if any two coils are energized with equal but opposite current, the field at the center will be zero. This equal and opposite current is realized by making the appropriate electrical interconnections between the inner and outer coils and applying current to the two coils using the same current source. In this example, the outermost coil 26 has exactly four times the diameter of the innermost coil 28, and has exactly four times as many turns. When magnetic susceptibility measurements are made using the outer coil 26, this coil is connected in series with the innermost coil 28, but with opposite polarity, as shown in FIG. 4 by the two oppositely directed arrows. The magnetic field cancels out almost completely at the location of the detector 10. The intermediate-diameter coil 30 has exactly twice the diameter, and twice the number of turns, as the innermost coil 28. When measurements are made using this intermediate coil 30, it is connected in series with the innermost coil to cancel out the magnetic field at the sensor 24 location.

The applied field coils 26,28,30 can comprise traces on a printed circuit board. To generate the maximum field for a given current magnitude, similar coil sets can be positioned on both sides of the circuit board 14, thus doubling the number of turns of each coil. In addition, stacks of circuit boards 14 can provide sufficiently strong field to the examined tissue sample, without the excessive ohmic heating (and the resulting undesirable thermal drifts) that can occur if too large a current is passed through a single circuit board. Alternatively, the printed circuit board can be replaced by wires, metal rods, or other electrical conductors supported by a rigid support structure that maintains the appropriate spatial relationship of the current carrying elements.

FIG. 5 shows a PC board 14 which has a number of circular holes for bolting individual boards together rigidly to a solid G-10 fiberglass plate for structural stability. The larger noncircular holes facilitate electrical connections between the coils 26,28,30 on the stacked circuit boards. A hole at the center of the coil set allows for placement of a sensor 24 in a low field region close to the sample. The magnetic sensor 24 is placed in the appropriate orientation so as to sense magnetic fields normal to the plane of the applied field coils (as indicated by FIG. 4). In this zero-field region, the sensor is practically immune to the applied field directly and only senses the body's response to the applied field.

In an example of the design shown in FIG. 5, the outer coil 26 consists of 16 equally spaced concentric loops with a mean diameter of 20 cm. The inner coil 28 consists of 4 equally spaced concentric loops with a mean diameter of 5 cm. The middle coil 30 has 8 equally spaced concentric loops with a mean diameter of 10 cm. The applied field coil design ensures that when any pair of coils is energized with equal and opposite current the applied field at the center of the coils is zero.

Measurements of liver iron concentration involving cryogenically cooled SQUID systems usually use a "water bag" to help discriminate the signal from the liver from that of the overlying abdominal tissue. The magnetic susceptibility of the liver ($1.6 \times 10^{-6}$ SI units) is only slightly different from that of the abdominal tissue (value close to that of water; $-9 \times 10^{-6}$ SI units). The susceptibility contrast between the liver and the abdominal tissue is typically smaller than that between the air and the abdominal tissue. Hence the liver will appear as an anomaly in the body which is itself an anomaly in the surrounding air space. In biomagnetic susceptibility measurements, the susceptibility contrast between the abdominal tissue and the air produces a magnetic response which interferes with the measurement of the response due to the liver iron itself. In order to minimize this interfering signal, a bag filled with water is positioned to fill the space between the sensor and the surface of the patient's abdomen. The water, whose magnetic susceptibility is nearly the same as that of the abdominal tissue, essentially removes any magnetic susceptibility contrast at the outer surface of the abdomen, as if the entire magnetic measurement were being made in an environment filled with material of a constant magnetic susceptibility approximately equal to that of the abdominal tissue. The magnetic susceptibility measurement then responds primarily to the magnetic susceptibility contrast between the liver and the surrounding abdominal tissue. This magnetic susceptibility anomaly is due almost entirely to the iron in the liver.

The room temperature instrument can also be used with a water bag, if necessary, to remove the interfering signal from the abdomen. Alternatively, the abdominal contribution to the signal can be measured and subtracted out by using the middle coil 30. Since the middle coil is smaller than the outer coil, the magnetic field generated by the middle coil will not penetrate as deeply into the body as will the field generated by the outer coil. Therefore, with the proper choice of coil dimensions, the response signal due to the applied field of the middle coil will be mostly due to the overlying abdominal tissue closer to the surface of the body, whereas the response signal due to the applied field of the outer coil will be due to both the liver and the abdominal tissue. Consequently, two successive magnetic susceptibility measurements, using the outer coil and the middle coil, provide two independent pieces of information, which can be used to solve mathematically for two unknown quantities, the magnetic susceptibilities of the liver tissue and the abdominal tissue. This method determines the magnetic susceptibility of the liver, while removing errors due to variability in the magnetic susceptibility of the abdominal tissue.

Ancillary Hardware and Method of Use

Figure 6:
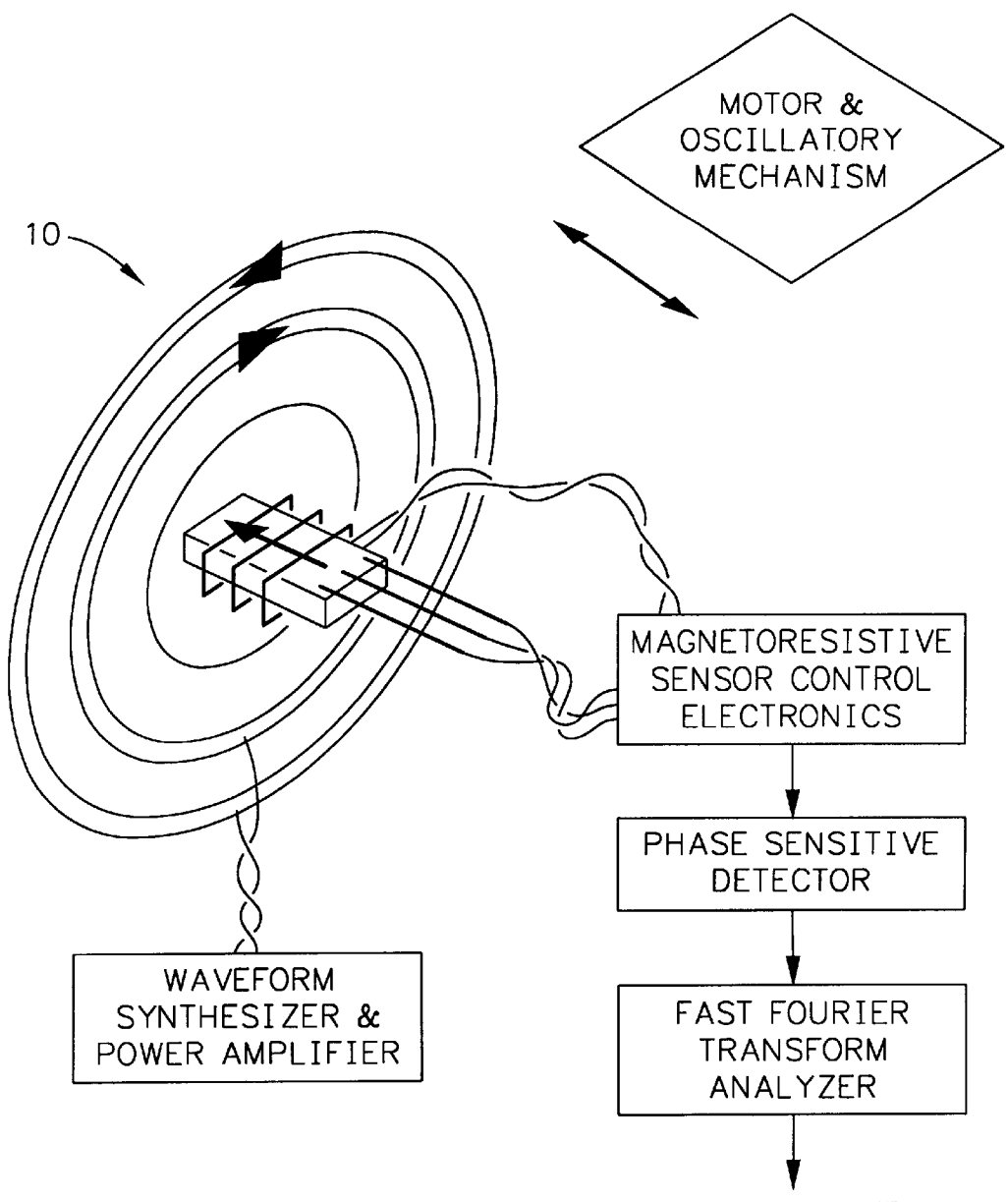

FIG. 6 shows the detector assembly 10 and the interface assembly components attached thereto. Preferably, an MR sensor can be used along with a feedback coil mounted on the sensor, which allows the sensor to be "locked" at its optimum operating point by applying a compensating field to cancel changes in the ambient field. This technique maintains constant sensitivity of the sensor. The detection assembly's MR sensor is part of a Wheatstone bridge wherein transduced resistance measurements are related to transduced sensed magnetic measurements. An electronic feedback circuit amplifies the voltage of the Wheatstone bridge, and supplies a feedback current to a small feedback coil wrapped around the MR sensor, compensating for changes in the ambient magnetic field and maintaining the sensing element at a constant magnetic field. In this "field-lock" scheme, the ambient magnetic field is actually measured by monitoring the current applied to the compensating coil by the feedback loop. This approach eliminates potential errors due to either the sensor's nonlinear response function or its temperature-dependent responsivity.

A phase sensitive detector measures the component of the output of the magnetic sensor that oscillates in phase with the AC applied field. A Fourier transform analyzer calculates the component of the output of the phase-sensitive detector that oscillates in phase with the modulation of the sample-sensor distance. This provides a way to distinguish the signal of interest from the low-frequency noise caused by thermal drifts. The function of the phase sensitive detector can be performed by a lockin amplifier, and the function of the Fourier transform analyzer can be performed by a spectrum analyzer. Preferably, either or both functions can be performed on a computer.

A signal source is used to generate an AC signal between 25 and 2 kHz. This signal, amplified by an audio frequency amplifier, provides a constant amplitude oscillating current through the applied field coils on the detection head assembly.

Figure 7:
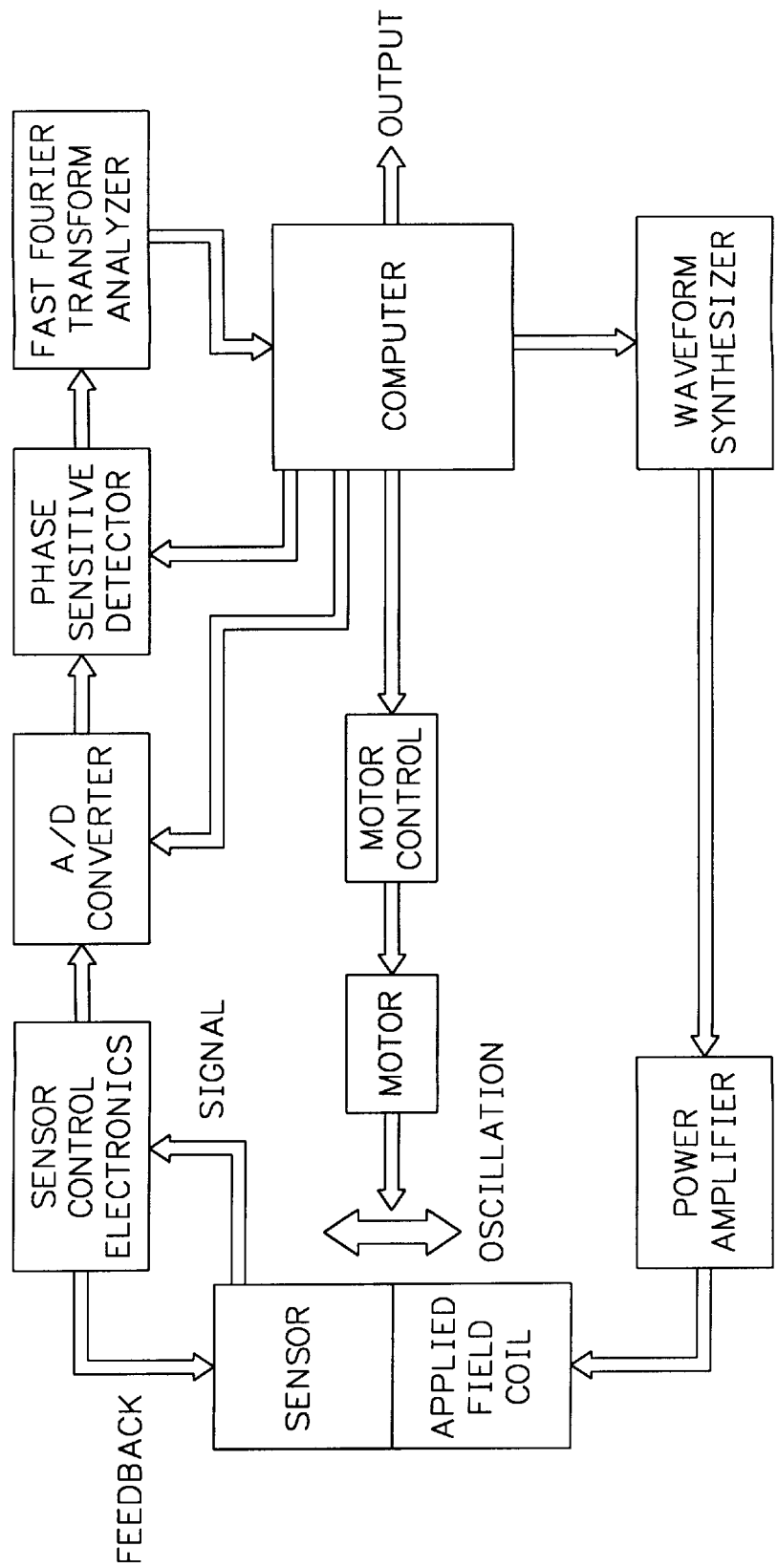
FIG. 7 shows a block diagram with the preferred applied field current source and analyzing components used in the probing instrument.

FIG. 7 shows the computer analyzer and control functions which process response signals from the sensor 24, and output information regarding the concentration of paramagnetic materials in body organs. In FIG. 7, the computer integrates and controls all instrument functions, including the modulation of the sensor-sample distance, the generation of the AC field coil current, and the processing of the magnetic sensor outputs to determine the magnetic susceptibility of the sample. The computer can be a personal computer with the required functioning signal cards and processors included. The motor indicated in FIG. 7 is preferably used to move the detector assembly towards and away from a patient's tissue area of interest. The fast Fourier transformer is used to resolve the variation of the received signal in synchrony with this motion. The waveform synthesizer is used to generate an AC signal, which is then amplified by the power amplifier to generate an AC current for the applied field coil. The waveform synthesizer function can be incorporated by the computer. The AC signal can have frequencies up to around 2,000 hertz, preferably avoiding harmonics of the power line frequency. The AC signal can be synchronized with the power lines, at a frequency commensurate with the power line frequency, in order to minimize noise due to the power lines.

Actual output from the computer can be a data storage device, a video display of useful medical information, or a connection to a computer system network.

Figure 8:
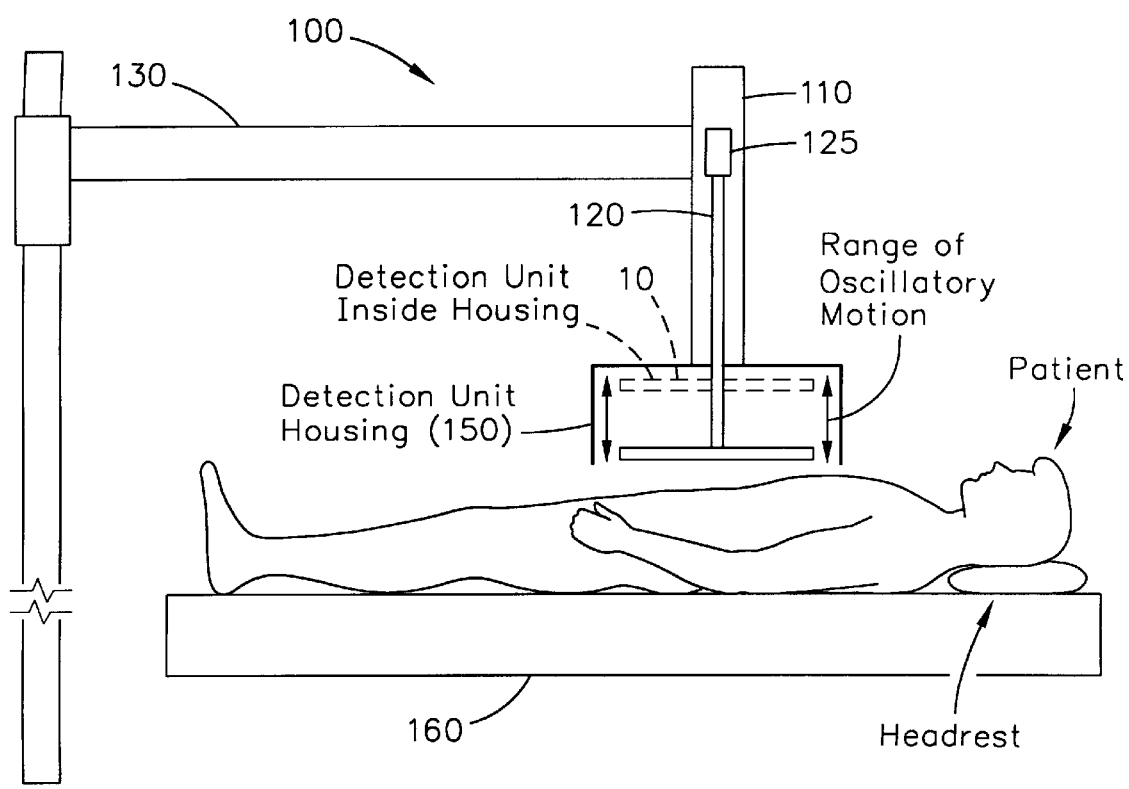
FIG. 8 shows and exemplary perspective view of the probing instrument.

The magnetic sensor control electronics, a motor/crank rod arrangement for oscillatory movement of the instrument's distal end detector assembly, a waveform synthesizer and power amplifier, a lock-in amplifier, and a spectrum analyzer or equivalent computer device for signal analysis can be incorporated in a single medical instrument unit as shown in exemplary form in FIG. 8 as unit 100. FIG. 8 shows the probe instrument 100 with an elongated positioning arm 130 wherein the detector assembly 10 is mounted at the distal end of the arm 110 which has a motor 125 within, with the required oscillatory drive members 120 that move the detector assembly 10 towards and away from a patient.

FIG. 8 shows the patient on a non-metallic table. The detector assembly 10 is positioned over a tissue area of interest, such as the patient's abdomen region where the liver is located. The detector assembly 10 has the sensor mounted to a reciprocating member 120 located within the arm 110 that moves the detector assembly 10 translationally towards and away from the distal end of the head member, preferably between one and six inches. The reciprocating action typically is in a range between around 0.5 to 10 hertz such that modulation of the detector assembly 10 filters out signal noise caused by temperature drifts in the applied field coils.

The reciprocating member 120 within the arm of the probe instrument 100 allows modulation of the distance between the examined tissue and the detector assembly 10, as explained above. The reciprocating member is made of nonmagnetic materials. In use, a water bag (not shown) may be placed between the detector assembly 10 and the patient.

Analysis is performed on the signal detected by the sensor to provide output information corresponding to the magnetic susceptibility of the liver. The concentration of iron in the liver can then be calculated from well established studies that directly relate liver iron susceptibility with liver iron concentration. The output of the instrument, in the form of liver iron concentration, can be displayed in ranges that extend as low as 30 micrograms per milliliter and as high as the highest concentration found in patients with severe iron overload.

Variations to the invention include the following:

Modulation of the distance between the sample and the detector assembly can improve the signal-to-noise ratio of magnetic susceptibility measurements on any type of sample (i.e., including samples other than the human body).

Another variation to the invention includes the methods and apparatus described in the parent U.S. patent application Ser. No. 08/670,393, wherein modulation of the sample-sensor distance will improve the signal-to-noise ratio of magnetic susceptibility measurements for the detection of ferromagnetic foreign bodies (FFBs) within the eye, brain, or body of a patient.

The instant invention describes an applied-field coil configuration, as shown in FIG. 5, consisting of two concentric circular loops carrying currents in opposite directions, in which the diameters and number of turns in the two loops are adjusted so as to cancel the magnetic field at the common center of the two coils. This applied-field coil design may be used in other types of magnetic susceptibility measurements.

In particular, the concentric-loop coil design (FIG. 5) may be used with the apparatus and methods described in the parent U.S. patent application Ser. No. 08/670,393, for the detection of ferromagnetic foreign bodies (FFBs) within the eye, brain, or body of a patient. The use of the concentric-loop coil would increase the magnetic susceptibility response of FFBs located deep below the surface of the patient's face, head, or body.

For the detection of FFBs in the eye, brain, or body, the parent U.S. patent application Ser. No. 08/670,393 teaches the measurement of appropriate magnetic-field gradients, or alternatively, the mapping of the magnetic-susceptibility response as a function of position, in order to compute the location of the FFB within the host. This spatial mapping or magnetic gradient measurement may be achieved either by using an array of more than one magnetic sensor, or by using a single magnetic sensor and moving the detection unit (applied field coils and magnetic sensor). Either approach may be used in conjunction with the concentric-loop applied field coil design shown in FIG. 5.

The applied-field coil design of FIG. 5 may be modified to accommodate an array of more than one magnetic sensor. The parent U.S. patent application Ser. No. 08/670,393 discloses that to reduce the noise produced by variations in the applied magnetic field, it is desirable to ensure that the applied magnetic field is as small as possible at the location of each magnetic sensor. The concentric-loop coil described above cancels the magnetic field at a single point, the common center of the at least two concentric loops. If the radius of the inner coil is decreased slightly in relation to that of the outer coil, or if the current in the inner coil is increased slightly in relation to that of the outer coil, the magnetic field will be canceled not at a single point, but along a circle concentric with the two loops. Multiple sensors may then be placed at different locations on this circle, and the applied magnetic field will be canceled out at the location of each sensor. This arrangement makes possible the simultaneous measurement of the magnetic field response at multiple points in space.

As an alternative, the noise produced by applied-field variations may be minimized by measuring differences in magnetic field between two or more magnetic sensors, as long as the magnetic sensors are positioned within the applied-field coils in such a way that the applied magnetic field is the same for each of the sensors. Such a result may be achieved with an applied field coil consisting of a circular loop, or multiple concentric loops, by placing each of the magnetic sensors at the same distance from the center of the loop(s).

Moreover, the applied field coils of the concentric coil design shown in FIGS. 4 and 5 can have differing dimensions and configurations to measure at other tissue regions in the body. Also, switchable configurations of the applied field coil connections can be controlled by the instrument's computer allowing for adaptive control of the instrument for multiple examining capabilities.

The proposed probe instrument allows for precision determination of concentration of paramagnetic materials in a body organ, in particular the liver. Several embodiments of the invention have been described above. It is likely that modifications and improvements will occur to those skilled in this technical field which are within the scope of the appended claims.

What is claimed is:

1. A method for noninvasive determination of magnetic susceptibility variation in a human body by measuring magnetic susceptibilities of tissue, the method comprising:
   providing an instrument which includes at least one magnetic sensor, an applied field coil and a current source connected to the applied field coil and means for processing sensed signals from the at least one magnetic sensor, wherein the instrument functionally operates at room temperature and minimizes noise due to temperature fluctuations at the magnetic sensor;
   positioning the instrument external to the patient in proximity to the tissue of interest;
   supplying the applied field coil with current thereby applying a magnetic field to the tissue of interest;
   sensing a response from the tissue of interest with the instrument; and
   outputting data corresponding to the magnetic susceptibility variation in the tissue.

2. The method recited in claim 1, wherein the supplying of current to the applied field coil comprises alternating current operating between about 25 to 2,000 hertz.

3. The method recited in claim 1, wherein the method further comprises providing the instrument with displacement means for displacing the magnetic sensor and the applied field coil simultaneously thereby compensating for noise introduced to the sensed signals.

4. The method recited in claim 3, wherein the displacement means operates between about one to six inches.

5. The method recited in claim 3, wherein the displacement means operates between about 0.5 to 10.0 hertz.

6. The method recited in claim 1, wherein the outputting of data corresponding to the magnetic susceptibility variation in the human body comprises concentrations of paramagnetic material in the tissue of interest.

7. The method recited in claim 6, wherein the paramagnetic material is iron and the tissue of interest is a liver.

8. The method recited in claim 7, wherein the outputting of data corresponds to concentrations of iron in the liver and the resolution of the measurements corresponds to 30 micrograms per milliliter.

9. An apparatus for noninvasively measuring magnetic susceptibility variations in body tissue to determine a compositional state in the body, the apparatus comprising:
   a detector assembly that includes:
      at least one magnetic sensor and an applied field coil for generating a magnetic field;
      a current signal generating source which connects to the applied field coil;
      a means for processing signals from the at least one magnetic sensor of observed magnetic susceptibility variations in body tissue; and
      a means for outputting data corresponding to a compositional state in the body;
   wherein the detector assembly functionally operates at room temperature and minimizes noise due to temperature fluctuations at the magnetic sensor.

10. The apparatus recited in claim 9, wherein the current signal generating source provides alternating current (AC) and operates between about 25 to 2,000 hertz and avoiding power line frequency and harmonics thereof.

11. The apparatus recited in claim 9, wherein the means for processing signals from the at least one magnetic sensor comprises a processor for analyzing the signals obtained from the magnetic sensor.

12. The apparatus recited in claim 9, wherein the means for processing signals further comprises outputting means for displaying paramagnetic material concentration.

13. The apparatus recited in claim 12, wherein the paramagnetic material is iron.

14. The apparatus recited in claim 9, wherein the applied field coil is designed to create a first zone of a finite magnetic field, within a selected region of the body, and a second zone of substantially zero magnetic field, outside the selected region; and
   the at least one magnetic sensor is positioned within said second zone of substantially zero magnetic field.

15. The apparatus recited in claim 14, wherein the applied field coil comprises two parallel flat coils and a connecting circuit between the two parallel coils causing current to flow in identical directions at corresponding locations in the two flat coils, thereby simulating parallel uniform sheets of current.

16. The apparatus recited in claim 14, wherein the excitation field coil comprises at least two concentric coils and a connecting circuit between the at least two concentric coils causing current to flow in opposite directions, thereby canceling the effects of a magnetic field caused by current flowing through the applied field coil at a central region of the at least two concentric coils.

17. The apparatus recited in claim 16, wherein the largest concentric coil has a diameter between around 15 to 50 centimeters.

18. The apparatus recited in claim 16, wherein there are at least three concentric coils, the outermost coils include at least two coils which are alternatively switched with the current source, whereby sufficient information can be derived independently as to the susceptibility of a deep lying tissue area in the body compared to a corresponding surface tissue area.

19. The apparatus recited in claim 18, wherein the deep lying tissue area is the liver and the overlying surface tissue area is abdominal tissue.

20. The apparatus recited in claim 16, wherein the current in each concentric coil is the same.

21. The apparatus recited in claim 14, wherein the detector assembly is multiple stacked applied field coils.

22. The apparatus recited in claim 9, wherein the at least one magnetic sensor attaches to a central region relative to the applied field coil.

23. The apparatus recited in claim 22, wherein the applied field coil is attached to a planar substrate.

24. The apparatus recited in claim 9, wherein the at least one magnetic sensor is a magnetoresistive sensor.

25. The apparatus recited in claim 24, wherein the at least one magnetoresistive sensor is part of a Wheatstone bridge sensing circuit.

26. The apparatus recited in claim 25, further including magnetic sensor compensating electronics and a feedback coil disposed about the magnetoresistive sensor for locking an optimum operating point by applying a compensating electrical current from compensating electronics to the feedback coil thereby maintaining constant measurement sensitivity of the apparatus.

27. The apparatus recited in claim 9, wherein the at least one magnetic sensor is a fluxgate sensor.

28. The apparatus recited in claim 9, wherein the at least one magnetic sensor is a magnetoinductive sensor.

29. The apparatus recited in claim 9, wherein the detector assembly further comprises a means for oscillating the detector assembly.

30. The apparatus recited in claim 29, wherein the detector assembly is housed in a housing structure for positioning the detector assembly in proximity to a surface of the human body, and the means for oscillating the detector assembly comprises a motor with attached drive members that move the detector assembly.

31. A magnetic susceptibility detector device comprising:
   an applied field coil configured to connect to a current source, the field coil being designed to create a first zone of a finite magnetic field, within a selected region of an observed specimen, and a second zone of substantially zero magnetic field, outside said selected region, the applied field coil having at least two concentric electric current carrying coils of conductor material; and
   a sensing device which is at least one magnetic sensor, the at least one sensor being positioned within said second zone of substantially zero magnetic field.

32. The device recited in claim 31, wherein the at least one magnetic sensor is a magnetoresistive sensor.

33. The device recited in claim 31, wherein the at least one magnetic sensor is a fluxgate sensor.

34. The device recited in claim 31, wherein the at least one magnetic sensor is a magnetoinductive sensor.

35. An apparatus for noninvasively determining magnetic susceptibility variation in body tissue, the apparatus comprising:
   a detector assembly that includes:
      at least one magnetic sensor and an applied field coil for generating a magnetic field, wherein the applied field coil is designed to create a first zone of a finite magnetic field, within a selected region of the body, and a second zone of substantially zero magnetic field, outside the selected region;
      the at least one magnetic sensor is positioned within said second zone of substantially zero magnetic field; and
      a means for oscillating the detector assembly:
      the detector assembly attaches to said means for oscillating the detector assembly;
      a current signal generating source which connects to the applied field coil; and
      a means for processing signals from the at least one magnetic sensor of observed magnetic susceptibility variation in the body;
      wherein the detector assembly functionally operates at room temperature and minimizes noise due to temperature fluctuations at the magnetic sensor.

36. The apparatus recited in claim 35, wherein the magnetic sensor attaches to a central region relative to the applied field coil.

37. The apparatus recited in claim 35, wherein the applied field coil includes two parallel flat coils and a connecting circuit between the two parallel coils causing current to flow in identical directions at corresponding locations in the two flat coils, thereby simulating parallel uniform sheets of current.

38. The apparatus recited in claim 35, wherein the excitation field coil comprises at least two concentric coils and a connecting circuit between the at least two concentric coils causing current to flow in opposite directions, thereby canceling the effects of a magnetic field caused by current flowing through the applied field coil at a central region of the at least two concentric coils.

39. The apparatus recited in claim 35, wherein the detector assembly is multiple stacked applied field coils.

40. The apparatus recited in claim 35, wherein the at least one magnetic sensor is a magnetoresistive sensor; the sensor forms part of a Wheatstone bridge circuit and further includes a means for compensating the magnetic sensor for locking an optimal operational state by applying a compensating electrical current from the compensating means thereby maintaining sensitivity of the apparatus.

41. The apparatus recited in claim 35, wherein the at least one magnetic sensor is a fluxgate sensor.

42. The apparatus recited in claim 35, wherein the at least one magnetic sensor is a magnetoinductive sensor.

* * * * *